United States Patent [19]

Briles et al.

[11] Patent Number: 5,679,768

[45] Date of Patent: Oct. 21, 1997

[54] EPITOPIC REGIONS OF PNEUMOCOCCAL SURFACE PROTEIN A

[75] Inventors: David E. Briles; Janet L. Yother, both of Birmingham, Ala.

[73] Assignee: UAB Research Foundation, Birmingham, Ala.

[21] Appl. No.: 465,746

[22] Filed: Jun. 6, 1995

Related U.S. Application Data

[63] Continuation of Ser. No. 48,896, Apr. 20, 1993, abandoned, which is a continuation-in-part of Ser. No. 835,698, Feb. 12, 1992, abandoned, which is a continuation-in-part of Ser. No. 656,773, Feb. 15, 1991, abandoned.

[51] Int. Cl.$^6$ .................. C07K 14/315; A61K 39/09; A61K 38/16

[52] U.S. Cl. .................. 530/300; 530/324; 530/350; 530/825; 424/190.1; 424/197.11; 424/200.1; 424/244.1; 435/252.3

[58] Field of Search .................. 424/244.1, 190.1, 424/197.11, 200.1; 530/300, 324, 350, 825; 435/252.3

[56] References Cited

PUBLICATIONS

Waltman et al, "Variation in the molecular weight of PspA- (pneumococcal surface protein A) among Streptococcus pneumoniae", Microbial Pathogenesis 1990; 8:61–69.
Waltman et al, Microbial Pathogenesis 1988, vol. 5: pp. 159–167.
Cohen et al, Science 1994, 263:488–489.
Engel et al, EMBO 1992,11:4369–4378.
Cohen et al, 1990, Proteins 7:1–15.
Fishetti et al, 1990, Molec. Micro. 4:1603–1605.
Young and Davis PNAS 80: 1194–1198 Mar. 1983.
"Antibodies, A Laboratory Manual", E. Harlow et al (Ed) See Chapter 13 pp. 514–551.
Pongor et al. Methods in Enzymology 154:450–473. 1987.
McDaniel et al (I), J.Exp.Med. 160:386–397, 1984.
McDaniel et al (II), Microbial Pathogenesis 1:519–531, 1986.
McDaniel et al (III), J.Exp.Med. 165:381–394, 1987.
McDaniel et al (IV), Infect. Immun., 59:222–228, 1991.
Crain et al, Infect. Immun., 58:3293–3299, 1990.
Abstracts of 89th Annual Meeting of the American Society for Microbiology, P.125, item D–257, May 1989.
Abstracts of 90th Annual Meeting of the American Society for Microbiology, p. 98, item D–106, May 1990.
Abstracts of 3rd International ASM Conference on Streptococcal Genetics, p.11, item 12, Jun. 1990.
Talkington et al, Infect. Immun. 59:1285–1289, 1991.
Yother et al, J. Bacteriol. 174:601–609, 1992.
Yother et al, J. Bacteriol. 174:610–618, 1992.
McDaniel et al (V), Microbiol Pathogenesis, 13:261–268; 1992.
Stover et al. "New use of BCG for recombinant vaccines" Nature (351)456–460, Jun. 1991.

Primary Examiner—Anthony C. Caputa
Attorney, Agent, or Firm—Curtis Morris & Safford P C

[57] ABSTRACT

A region of the PspA protein of the Rx1 strain of *Streptococus pneumoniae* has been identified as containing protection-eliciting epitopes which are cross-reactive with PspAs of other *S.pneumoniae* strains. The region comprises the 68-amino acid sequence extending from amino acid residues 192 to 260 of the Rx1 PspA strain.

11 Claims, 6 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2085 base pairs
( B ) TYPE: nucleic acid
( C ) STRANDEDNESS: double
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: Streptococcus pneumoniae
( B ) STRAIN: Rx1

( v i i ) IMMEDIATE SOURCE:
( B ) CLONE: JY4313

( i x ) FEATURE:
( A ) NAME/KEY: intron
( B ) LOCATION: 1..2085

( i x ) FEATURE:
( A ) NAME/KEY: CDS
( B ) LOCATION: join(127..1984)

( x i ) SEQUENCE DESCRIPTION: SEQ ID NO:1:

```
AAGCTTATGA TATAGAAATT TGTAACAAAA ATGTAATATA AAACACTTGA CAAATATTTA        60

CGGAGGAGGC TTATACTTAA TATAAGTATA GTCTGAAAAT GACTATCAGA AAAGAGGTAA       120

ATTTAG ATG AAT AAG AAA AAA ATG ATT TTA ACA AGT CTA GCC AGC GTC          168
       Met Asn Lys Lys Lys Met Ile Leu Thr Ser Leu Ala Ser Val
         1               5                  10

CCT ATC TTA GGG GCT GGT TTT GTT GCG TCT CAG CCT ACT GTT GTA AGA         216
Ala Ile Leu Gly Ala Gly Phe Val Ala Ser Gln Pro Thr Val Val Arg
 15              20                  25                  30

GCA GAA GAA TCT CCC GTA GCC AGT CAG TCT AAA GCT GAG AAA GAC TAT         264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT         312
Asp Ala Ala Lys Lys Asp Ala Lys Asn Ala Lys Lys Ala Val Glu Asp
                 50                  55                  60

GCT CAA AAG GCT TTA GAT GAT GCA AAA GCT GCT CAG AAA AAA TAT GAC         360
Ala Gln Lys Ala Leu Asp Asp Ala Lys Ala Ala Gln Lys Lys Tyr Asp
             65                  70                  75

GAG GAT CAG AAG AAA ACT GAG GAG AAA GCC GCG CTA GAA AAA GCA GCG         408
Glu Asp Gln Lys Lys Thr Glu Glu Lys Ala Ala Leu Glu Lys Ala Ala
         80                  85                  90

TCT GAA GAG ATG GAT AAG GCA GTG GCA GCA GTT CAA CAA GCG TAT CTA         456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG         504
Ala Tyr Gln Gln Ala Thr Asp Lys Ala Ala Lys Asp Ala Ala Asp Lys
                 115                 120                 125

ATG ATA GAT GAA GCT AAG AAA CGC GAA GAA GAG GCA AAA ACT AAA TTT         552
Met Ile Asp Glu Ala Lys Lys Arg Glu Glu Glu Ala Lys Thr Lys Phe
                 130                 135                 140

AAT ACT GTT CGA GCA ATG GTA GTT CCT GAG CCA GAG CAG TTG GCT GAG         600
```

```
Asn Thr Val Arg Ala Met Val Val Pro Glu Pro Glu Gln Leu Ala Glu
        145                 150                 155

ACT AAG AAA AAA TCA GAA GAA GCT AAA CAA AAA GCA CCA GAA CTT ACT       648
Thr Lys Lys Lys Ser Glu Glu Ala Lys Gln Lys Ala Pro Glu Leu Thr
    160                 165                 170

AAA AAA CTA GAA GAA GCT AAA GCA AAA TTA GAA GAG GCT GAG AAA AAA       696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA       744
Ala Thr Glu Ala Lys Gln Lys Val Asp Ala Glu Glu Val Ala Pro Gln
                195                 200                 205

GCT AAA ATC GCT GAA TTG GAA AAT CAA GTT CAT AGA CTA GAA CAA GAG       792
Ala Lys Ile Ala Glu Leu Glu Asn Gln Val His Arg Leu Glu Gln Glu
            210                 215                 220

CTC AAA GAG ATT GAT GAG TCT GAA TCA GAA GAT TAT GCT AAA GAA GGT       840
Leu Lys Glu Ile Asp Glu Ser Glu Ser Glu Asp Tyr Ala Lys Glu Gly
        225                 230                 235

TTC CGT GCT CCT CTT CAA TCT AAA TTG GAT GCC AAA AAA GCT AAA CTA       888
Phe Arg Ala Pro Leu Gln Ser Lys Leu Asp Ala Lys Lys Ala Lys Leu
    240                 245                 250

TCA AAA CTT GAA GAG TTA AGT GAT AAG ATT GAT GAG TTA GAC GCT GAA       936
Ser Lys Leu Glu Glu Leu Ser Asp Lys Ile Asp Glu Leu Asp Ala Glu
255                 260                 265                 270

ATT GCA AAA CTT GAA GAT CAA CTT AAA GCT GCT GAA GAA AAC AAT AAT       984
Ile Ala Lys Leu Glu Asp Gln Leu Lys Ala Ala Glu Glu Asn Asn Asn
                275                 280                 285

GTA GAA GAC TAC TTT AAA GAA GGT TTA GAG AAA ACT ATT GCT GCT AAA      1032
Val Glu Asp Tyr Phe Lys Glu Gly Leu Glu Lys Thr Ile Ala Ala Lys
            290                 295                 300

AAA GCT GAA TTA GAA AAA ACT GAA GCT GAC CTT AAG AAA GCA GTT AAT      1080
Lys Ala Glu Leu Glu Lys Thr Glu Ala Asp Leu Lys Lys Ala Val Asn
        305                 310                 315

GAG CCA GAA AAA CCA GCT CCA GCT CCA GAA ACT CCA GCC CCA GAA GCA      1128
Glu Pro Glu Lys Pro Ala Pro Ala Pro Glu Thr Pro Ala Pro Glu Ala
    320                 325                 330

CCA GCT GAA CAA CCA AAA CCA GCG CCG GCT CCT CAA CCA GCT CCC GCA      1176
Pro Ala Glu Gln Pro Lys Pro Ala Pro Ala Pro Gln Pro Ala Pro Ala
335                 340                 345                 350

CCA AAA CCA GAG AAG CCA GCT GAA CAA CCA AAA CCA GAA AAA ACA GAT      1224
Pro Lys Pro Glu Lys Pro Ala Glu Gln Pro Lys Pro Glu Lys Thr Asp
                355                 360                 365

GAT CAA CAA GCT GAA GAA GAC TAT GCT CGT AGA TCA GAA GAA GAA TAT      1272
Asp Gln Gln Ala Glu Glu Asp Tyr Ala Arg Arg Ser Glu Glu Glu Tyr
            370                 375                 380

AAT CGC TTG ACT CAA CAG CAA CCG CCA AAA GCT GAA AAA CCA GCT CCT      1320
Asn Arg Leu Thr Gln Gln Gln Pro Pro Lys Ala Glu Lys Pro Ala Pro
        385                 390                 395

GCA CCA AAA ACA GGC TGG AAA CAA GAA AAC GGT ATG TGG TAC TTC TAC      1368
Ala Pro Lys Thr Gly Trp Lys Gln Glu Asn Gly Met Trp Tyr Phe Tyr
    400                 405                 410

AAT ACT GAT GGT TCA ATG GCG ACA GGA TGG CTC CAA AAC AAC GGT TCA      1416
Asn Thr Asp Gly Ser Met Ala Thr Gly Trp Leu Gln Asn Asn Gly Ser
415                 420                 425                 430

TGG TAC TAC CTC AAC AGC AAT GGT GCT ATG GCT ACA GGT TGG CTC CAA      1464
Trp Tyr Tyr Leu Asn Ser Asn Gly Ala Met Ala Thr Gly Trp Leu Gln
                435                 440                 445

TAC AAT GGT TCA TGG TAT TAC CTC AAC GCT AAC GGC GCT ATG GCA ACA      1512
Tyr Asn Gly Ser Trp Tyr Tyr Leu Asn Ala Asn Gly Ala Met Ala Thr
            450                 455                 460

GGT TGG GCT AAA GTC AAC GGT TCA TGG TAC TAC CTC AAC GCT AAT GGT      1560
```

| | | | | | | | | | | | | | | | |
|---|---|---|---|---|---|---|---|---|---|---|---|---|---|---|---|
| Gly | Trp | Ala<br>465 | Lys | Val | Asn | Gly<br>470 | Ser | Trp | Tyr | Tyr | Leu | Asn<br>475 | Ala | Asn | Gly |
| GCT | ATG | GCT | ACA | GGT | TGG | CTC | CAA | TAC | AAC | GGT | TCA | TGG | TAT | TAC | CTC | 1608 |
| Ala | Met<br>480 | Ala | Thr | Gly | Trp | Leu<br>485 | Gln | Tyr | Asn | Gly | Ser<br>490 | Trp | Tyr | Tyr | Leu |
| AAC | GCT | AAC | GGC | GCT | ATG | GCA | ACA | GGT | TGG | GCT | AAA | GTC | AAC | GGT | TCA | 1656 |
| Asn<br>495 | Ala | Asn | Gly | Ala | Met<br>500 | Ala | Thr | Gly | Trp | Ala<br>505 | Lys | Val | Asn | Gly | Ser<br>510 |
| TGG | TAC | TAC | CTC | AAC | GCT | AAT | GGT | GCT | ATG | GCT | ACA | GGT | TGG | CTC | CAA | 1704 |
| Trp | Tyr | Tyr | Leu | Asn<br>515 | Ala | Asn | Gly | Ala | Met<br>520 | Ala | Thr | Gly | Trp | Leu<br>525 | Gln |
| TAC | AAC | GGT | TCA | TGG | TAC | TAC | CTC | AAC | GCT | AAC | GGT | GCT | ATG | GCT | ACA | 1752 |
| Tyr | Asn | Gly | Ser<br>530 | Trp | Tyr | Tyr | Leu | Asn<br>535 | Ala | Asn | Gly | Ala | Met<br>540 | Ala | Thr |
| GGT | TGG | GCT | AAA | GTC | AAC | GGT | TCA | TGG | TAC | TAC | CTC | AAC | GCT | AAT | GGT | 1800 |
| Gly | Trp | Ala<br>545 | Lys | Val | Asn | Gly | Ser<br>550 | Trp | Tyr | Tyr | Leu | Asn<br>555 | Ala | Asn | Gly |
| GCT | ATG | GCA | ACA | GGT | TGG | GTG | AAA | GAT | GGA | GAT | ACC | TGG | TAC | TAT | CTT | 1848 |
| Ala | Met<br>560 | Ala | Thr | Gly | Trp | Val<br>565 | Lys | Asp | Gly | Asp | Thr<br>570 | Trp | Tyr | Tyr | Leu |
| GAA | GCA | TCA | GGT | GCT | ATG | AAA | GCA | AGC | CAA | TGG | TTC | AAA | GTA | TCA | GAT | 1896 |
| Glu<br>575 | Ala | Ser | Gly | Ala | Met<br>580 | Lys | Ala | Ser | Gln | Trp<br>585 | Phe | Lys | Val | Ser | Asp<br>590 |
| AAA | TGG | TAC | TAT | GTC | AAT | GGT | TTA | GGT | GCC | CTT | GCA | GTC | AAC | ACA | ACT | 1944 |
| Lys | Trp | Tyr | Tyr | Val<br>595 | Asn | Gly | Leu | Gly | Ala<br>600 | Leu | Ala | Val | Asn | Thr<br>605 | Thr |
| GTA | GAT | GGC | TAT | AAA | GTC | AAT | GCC | AAT | GGT | GAA | TGG | GTT | TAA | GCC | GAT | 1992 |
| Val | Asp | Gly | Tyr<br>610 | Lys | Val | Asn | Ala | Asn<br>615 | Gly | Glu | Trp | Val | * | | |
| TAA | ATT | AAA | GCA | TGT | TAA | GAA | CAT | TTG | ACA | TTT | TAA | TTT | TGA | AAC | AAA | 2040 |
| GAT | AAG | GTT | CGA | TTG | AAT | AGA | TTT | ATG | TTC | GTA | TTC | TTT | AGG | TAC | | 2085 |

( 2 ) INFORMATION FOR SEQ ID NO:2:

( i ) SEQUENCE CHARACTERISTICS:
    ( A ) LENGTH: 619 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Asn | Lys | Lys | Lys<br>5 | Met | Ile | Leu | Thr | Ser<br>10 | Leu | Ala | Ser | Val | Ala<br>15 | Ile |
| Leu | Gly | Ala | Gly<br>20 | Phe | Val | Ala | Ser | Gln<br>25 | Pro | Thr | Val | Val | Arg<br>30 | Ala | Glu |
| Glu | Ser | Pro<br>35 | Val | Ala | Ser | Gln | Ser<br>40 | Lys | Ala | Glu | Lys | Asp<br>45 | Tyr | Asp | Ala |
| Ala | Lys | Lys<br>50 | Asp | Ala | Lys | Asn<br>55 | Ala | Lys | Lys | Ala | Val<br>60 | Glu | Asp | Ala | Gln |
| Lys | Ala<br>65 | Leu | Asp | Asp | Ala<br>70 | Lys | Ala | Ala | Gln | Lys<br>75 | Lys | Tyr | Asp | Glu | Asp<br>80 |
| Gln | Lys | Lys | Thr | Glu<br>85 | Glu | Lys | Ala | Ala | Leu<br>90 | Glu | Lys | Ala | Ala | Ser<br>95 | Glu |
| Glu | Met | Asp | Lys<br>100 | Ala | Val | Ala | Ala | Val<br>105 | Gln | Gln | Ala | Tyr | Leu<br>110 | Ala | Tyr |
| Gln | Gln | Ala<br>115 | Thr | Asp | Lys | Ala | Ala<br>120 | Lys | Asp | Ala | Ala | Asp<br>125 | Lys | Met | Ile |
| Asp | Glu | Ala | Lys | Lys | Arg | Glu | Glu | Glu | Ala | Lys | Thr | Lys | Phe | Asn | Thr |

-continued

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 130 |     |     |     | 135 |     |     |     | 140 |     |     |     |
| Val | Arg | Ala | Met | Val | Val | Pro | Glu | Pro | Glu | Gln | Leu | Ala | Glu | Thr | Lys |
| 145 |     |     |      | 150 |     |     |     | 155 |     |     |     |     |     |     | 160 |
| Lys | Lys | Ser | Glu | Glu | Ala | Lys | Gln | Lys | Ala | Pro | Glu | Leu | Thr | Lys | Lys |
|     |     |     |     | 165 |     |     |     | 170 |     |     |     |     |     | 175 |     |
| Leu | Glu | Glu | Ala | Lys | Ala | Lys | Leu | Glu | Glu | Ala | Glu | Lys | Lys | Ala | Thr |
|     |     |     | 180 |     |     |     |     | 185 |     |     |     |     | 190 |     |     |
| Glu | Ala | Lys | Gln | Lys | Val | Asp | Ala | Glu | Glu | Val | Ala | Pro | Gln | Ala | Lys |
|     |     | 195 |     |     |     |     | 200 |     |     |     |     | 205 |     |     |     |
| Ile | Ala | Glu | Leu | Glu | Asn | Gln | Val | His | Arg | Leu | Glu | Gln | Glu | Leu | Lys |
|     | 210 |     |     |     |     | 215 |     |     |     |     | 220 |     |     |     |     |
| Glu | Ile | Asp | Glu | Ser | Glu | Ser | Glu | Asp | Tyr | Ala | Lys | Glu | Gly | Phe | Arg |
| 225 |     |     |     |     | 230 |     |     |     |     | 235 |     |     |     |     | 240 |
| Ala | Pro | Leu | Gln | Ser | Lys | Leu | Asp | Ala | Lys | Lys | Ala | Lys | Leu | Ser | Lys |
|     |     |     |     | 245 |     |     |     |     | 250 |     |     |     |     | 255 |     |
| Leu | Glu | Glu | Leu | Ser | Asp | Lys | Ile | Asp | Glu | Leu | Asp | Ala | Glu | Ile | Ala |
|     |     |     | 260 |     |     |     |     | 265 |     |     |     |     | 270 |     |     |
| Lys | Leu | Glu | Asp | Gln | Leu | Lys | Ala | Ala | Glu | Glu | Asn | Asn | Asn | Val | Glu |
|     |     | 275 |     |     |     |     | 280 |     |     |     |     | 285 |     |     |     |
| Asp | Tyr | Phe | Lys | Glu | Gly | Leu | Glu | Lys | Thr | Ile | Ala | Ala | Lys | Lys | Ala |
|     | 290 |     |     |     |     | 295 |     |     |     |     | 300 |     |     |     |     |
| Glu | Leu | Glu | Lys | Thr | Glu | Ala | Asp | Leu | Lys | Lys | Ala | Val | Asn | Glu | Pro |
| 305 |     |     |     |     | 310 |     |     |     |     | 315 |     |     |     |     | 320 |
| Glu | Lys | Pro | Ala | Pro | Ala | Pro | Glu | Thr | Pro | Ala | Pro | Glu | Ala | Pro | Ala |
|     |     |     |     | 325 |     |     |     |     | 330 |     |     |     |     | 335 |     |
| Glu | Gln | Pro | Lys | Pro | Ala | Pro | Ala | Pro | Gln | Pro | Ala | Pro | Ala | Pro | Lys |
|     |     |     | 340 |     |     |     |     | 345 |     |     |     |     | 350 |     |     |
| Pro | Glu | Lys | Pro | Ala | Glu | Gln | Pro | Lys | Pro | Glu | Lys | Thr | Asp | Asp | Gln |
|     |     | 355 |     |     |     |     | 360 |     |     |     |     | 365 |     |     |     |
| Gln | Ala | Glu | Glu | Asp | Tyr | Ala | Arg | Arg | Ser | Glu | Glu | Tyr | Asn | Arg |     |
|     | 370 |     |     |     |     | 375 |     |     |     |     | 380 |     |     |     |     |
| Leu | Thr | Gln | Gln | Gln | Pro | Pro | Lys | Ala | Glu | Lys | Pro | Ala | Pro | Ala | Pro |
| 385 |     |     |     |     | 390 |     |     |     |     | 395 |     |     |     |     | 400 |
| Lys | Thr | Gly | Trp | Lys | Gln | Glu | Asn | Gly | Met | Trp | Tyr | Phe | Tyr | Asn | Thr |
|     |     |     |     | 405 |     |     |     |     | 410 |     |     |     |     | 415 |     |
| Asp | Gly | Ser | Met | Ala | Thr | Gly | Trp | Leu | Gln | Asn | Asn | Gly | Ser | Trp | Tyr |
|     |     |     | 420 |     |     |     |     | 425 |     |     |     |     | 430 |     |     |
| Tyr | Leu | Asn | Ser | Asn | Gly | Ala | Met | Ala | Thr | Gly | Trp | Leu | Gln | Tyr | Asn |
|     |     | 435 |     |     |     |     | 440 |     |     |     |     | 445 |     |     |     |
| Gly | Ser | Trp | Tyr | Tyr | Leu | Asn | Ala | Asn | Gly | Ala | Met | Ala | Thr | Gly | Trp |
|     | 450 |     |     |     |     | 455 |     |     |     |     | 460 |     |     |     |     |
| Ala | Lys | Val | Asn | Gly | Ser | Trp | Tyr | Tyr | Leu | Asn | Ala | Asn | Gly | Ala | Met |
| 465 |     |     |     |     | 470 |     |     |     |     | 475 |     |     |     |     | 480 |
| Ala | Thr | Gly | Trp | Leu | Gln | Tyr | Asn | Gly | Ser | Trp | Tyr | Tyr | Leu | Asn | Ala |
|     |     |     |     | 485 |     |     |     |     | 490 |     |     |     |     | 495 |     |
| Asn | Gly | Ala | Met | Ala | Thr | Gly | Trp | Ala | Lys | Val | Asn | Gly | Ser | Trp | Tyr |
|     |     |     | 500 |     |     |     |     | 505 |     |     |     |     | 510 |     |     |
| Tyr | Leu | Asn | Ala | Asn | Gly | Ala | Met | Ala | Thr | Gly | Trp | Leu | Gln | Tyr | Asn |
|     |     | 515 |     |     |     |     | 520 |     |     |     |     | 525 |     |     |     |
| Gly | Ser | Trp | Tyr | Tyr | Leu | Asn | Ala | Asn | Gly | Ala | Met | Ala | Thr | Gly | Trp |
|     | 530 |     |     |     |     | 535 |     |     |     |     | 540 |     |     |     |     |
| Ala | Lys | Val | Asn | Gly | Ser | Trp | Tyr | Tyr | Leu | Asn | Ala | Asn | Gly | Ala | Met |
| 545 |     |     |     |     | 550 |     |     |     |     | 555 |     |     |     |     | 560 |

| Ala | Thr | Gly | Trp | Val 565 | Lys | Asp | Gly | Asp | Thr 570 | Trp | Tyr | Tyr | Leu | Glu 575 | Ala |
|---|---|---|---|---|---|---|---|---|---|---|---|---|---|---|---|
| Ser | Gly | Ala | Met 580 | Lys | Ala | Ser | Gln | Trp 585 | Phe | Lys | Val | Ser | Asp 590 | Lys | Trp |
| Tyr | Tyr | Val 595 | Asn | Gly | Leu | Gly | Ala 600 | Leu | Ala | Val | Asn | Thr 605 | Thr | Val | Asp |
| Gly | Tyr 610 | Lys | Val | Asn | Ala | Asn 615 | Gly | Glu | Trp | Val | | | | | |

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

GCGCGTCGAC GGCTTAAACC CATTCACCAT TGG 33

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

CCGGATCCTG AGCCAGAGCA GTTGGCTG 28

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

CCGGATCCGC TCAAAGAGAT TGATGAGTCT G 31

EPITOPIC REGIONS OF PNEUMOCOCCAL SURFACE PROTEIN A

REFERENCE TO RELATED APPLICATION

This application is a continuation of application Ser. No. 08/048,896, filed Apr. 20, 1993, now abandoned which is a continuation-in-part application of application Ser. No. 07/835,698, filed Feb. 12, 1992; now abandoned and continuation-in-part application of application Ser. No. 07/656,773, filed Feb. 15, 1991, now abandoned.

FIELD OF INVENTION

This invention relates to recognition of epitopic regions of pneumococcal surface protein A (PspA), the major virulence factor of Streptococcus pneumoniae.

BACKGROUND TO THE INVENTION

Streptococcus pneumoniae is an important cause of otitis media, meningitis, bacteremia and pneumonia. Despite the use of antibiotics and vaccines, the prevalence of pneumococcal infections has declined little over the last twenty-five years.

It is generally accepted that immunity to Streptococcus pneumoniae can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to proteins to make them immunogenic. This approach has been successful, for example, with Haemophilus influenzae b (see U.S. Pat. No. 4,496,538 to Gordon and U.S. Pat. No. 4,673,574 to Anderson). However, there are over eighty known capsular serotypes of S. pneumoniae of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults. Furthermore, such a vaccine would probably be much more expensive to produce than any of the other childhood vaccines in routine use.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J.Exp.Med. 160:386–397, 1984, there is described the production of hybridoma antibodies that recognize cell surface proteins on S. pneumoniae and protection of mice from infection with certain strains of encapsulated pneumococci by such antibodies. This surface protein antigen has been termed "pneumococcal surface protein A" or PspA for short.

In McDaniel et al (II), Microbial Pathogenesis 1:519–531, 1986, there are described studies on the characterization of the PspA. From the results of McDaniel (II), McDaniel (III), J.Exp. Med. 165:381–394, 1987, Waltman et al., Microb. Pathog. 8:61–69, 1990 and Crain et al., Infect. Immun. 58:3293–3299, 1990, it was also apparent that the PspAs of different strains frequently exhibit considerable diversity in terms of their epitopes, and apparent molecular weight.

In McDaniel et al (III), there is disclosed that immunization of X-linked immunodeficient (XID) mice with non-encapsulated pneumococci expressing PspA, but not isogenic pneumococci lacking PspA, protects mice from subsequent fatal infection with pneumococci.

In McDaniel et al (IV), Infect. Immun., 59:222–228, 1991, there is described immunization of mice with a recombinant full length fragment of PspA that is able to elicit protection against pneumococcal strains of capsular types 6A and 3.

In Crain et al, (supra) there is described a rabbit antiserum that detects PspA in 100% (n=95) of clinical and laboratory isolates of strains of S. pneumoniae. When reacted with seven monoclonal antibodies to PspA, fifty-seven S. pneumoniae isolates exhibited thirty-one different patterns of reactivity. Accordingly, although a large number of serologically-different PspAs exist, there are extensive cross-reactions between PspAs.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant λ gt11 clone, elicited protection against challenge with several S. pneumoniae strains representing different capsular and PspA types, as described in McDaniel et al (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of S. pneumoniae strains.

In addition to the published literature specifically referred to above, the inventors, in conjunction with coworkers, have published further details concerning PspA's, as follows:
1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al (I), J. Bacteriol. 174:601–609, 1992;
6. Yother et al (II), J. Bacteriol. 174:610–618, 1992; and
7. McDaniel et al (V), Microbiol Pathogenesis, 13:261–268.

In the aforementioned copending United States patent applications Ser. Nos. 656,773, now abandoned and 835, 698, now abandoned as well as in Yother et al (I) and (II), there are described the preparation of mutants of S. pneumomiae that secrete an immunogenic truncated form of the PspA protein, and the isolation and purification of the secreted protein. The truncated form of PspA was found to be immunoprotective and to contain the protective epitopes of PspA. The PspA protein described therein is soluble in physiologic solution and lacks at least the functional cell membrane anchor region.

In the specification which follows and the drawings accompanying the same, there are utilized certain accepted abbreviations with respect to the amino acids represented thereby. The following Table I identifies those abbreviations:

TABLE I

AMINO ACID ABBREVIATIONS

| | |
|---|---|
| A = Ala = Alanine | M = Met = Methionine |
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |
| G = Gly = Glycine | S = Ser = Serine |
| H = His = Histidine | T = Thr = Threonine |
| I = Ile = Isoleucine | V = Val = Valine |
| K = Lys = Lysine | W = Try = Tryptophan |
| L = Leu = Leucine | Y = Tyr = Tyrosine |

SUMMARY OF INVENTION

In accordance with the present invention, there has been identified a 68-amino acid region of PspA from the Rx1 strain of *Streptococcus pneumoniae* which not only contains protection-eliciting epitopes, but also is sufficiently cross-reactive with other PspA's from other *S. pneumoniae* strains so as to be a suitable candidate for the region of PspA to be incorporated into a recombinant PspA vaccine.

The 68-amino acid sequence extends from amino acid residues 192 to 260 of the Rx1 PspA protein. While the disclosure herein refers specifically to the specific 68 amino acid sequence of the Rx1 PspA protein, any region of a PspA protein from any other *S. pneumoniae* strains which is homologous to this sequence of the Rx1 PspA protein is included within the scope of the invention, for example, from strains D39 and R36A.

Accordingly, in one aspect, the present invention provides an isolated PspA protein fragment comprising amino acid residues 192 to 260 of the PspA protein of the Rx1 strain of *Streptococcus pneumoniae* and containing at least one protection-eliciting epitope.

The protein fragment may be one containing an amino acid sequence corresponding to or homologous to the amino acid residues 192 to 260 of the PspA protein of the Rx1 strain and hence may comprise fragments larger than ones containing the specific amino acid sequence.

The protein fragment of the invention may be produced recombinantly in the form of a truncated C-terminal deleted product containing the protein fragment, specifically a truncated C-terminal-deleted product containing the approximately C-terminal third of an α-helical region of the native PspA protein.

The present invention also includes an isolated protein fragment comprising an amino acid sequence corresponding to that of a protein-eliciting epitope contained in amino acid residues 192 to 260 of the PspA protein of the Rx1 strain of Streptococcus pneumoniae.

BRIEF DESCRIPTION OF DRAWINGS

FIGS. 1A–C contains the DNA sequence for the pspA gene of the Rx1 strain of *S. pneumoniae* with the deduced amino acid sequence for the PspA protein (SEQ ID NOS: 1 and 2);

GENERAL DESCRIPTION OF INVENTION

Figure 1A:
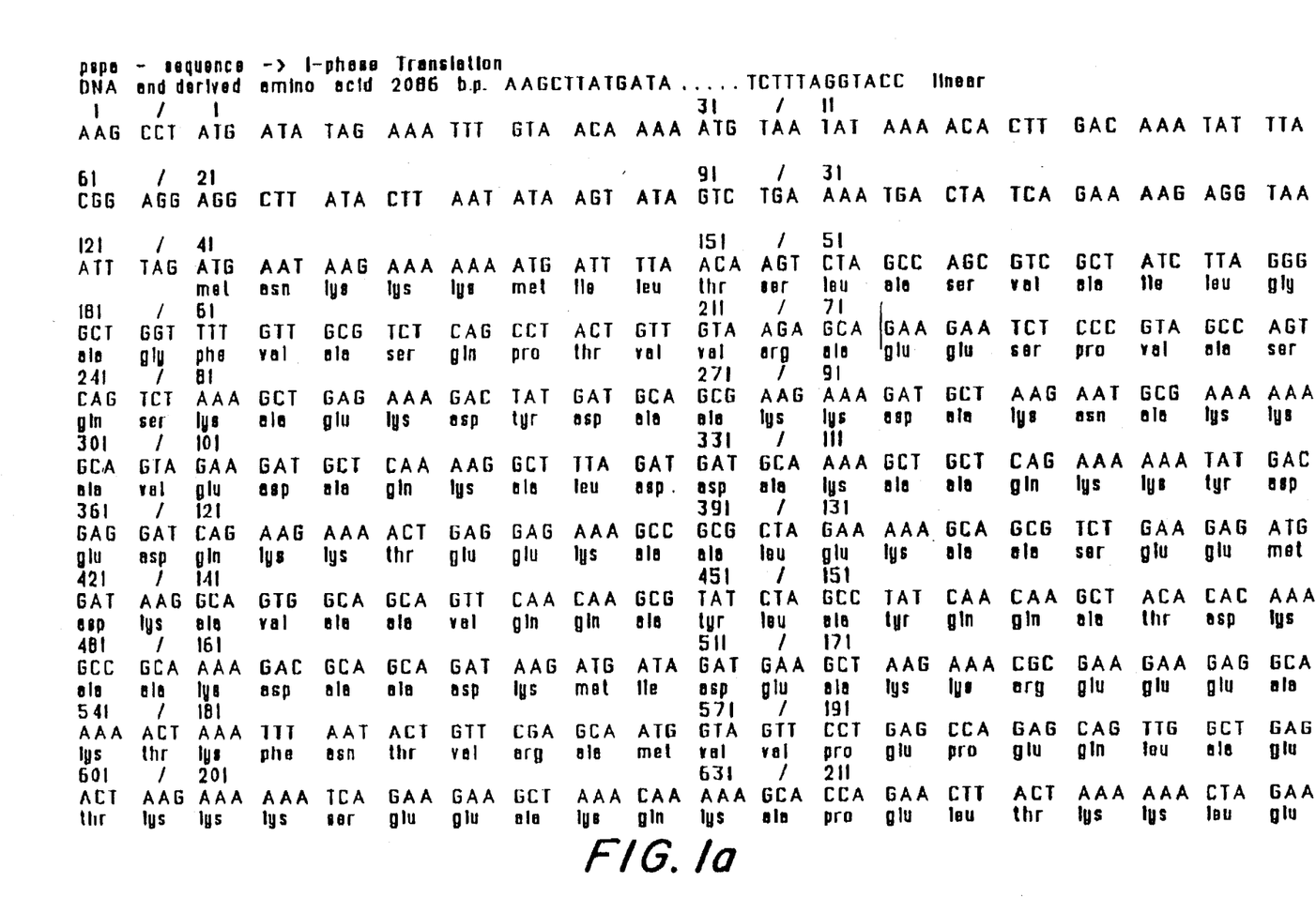
Figure 1B:
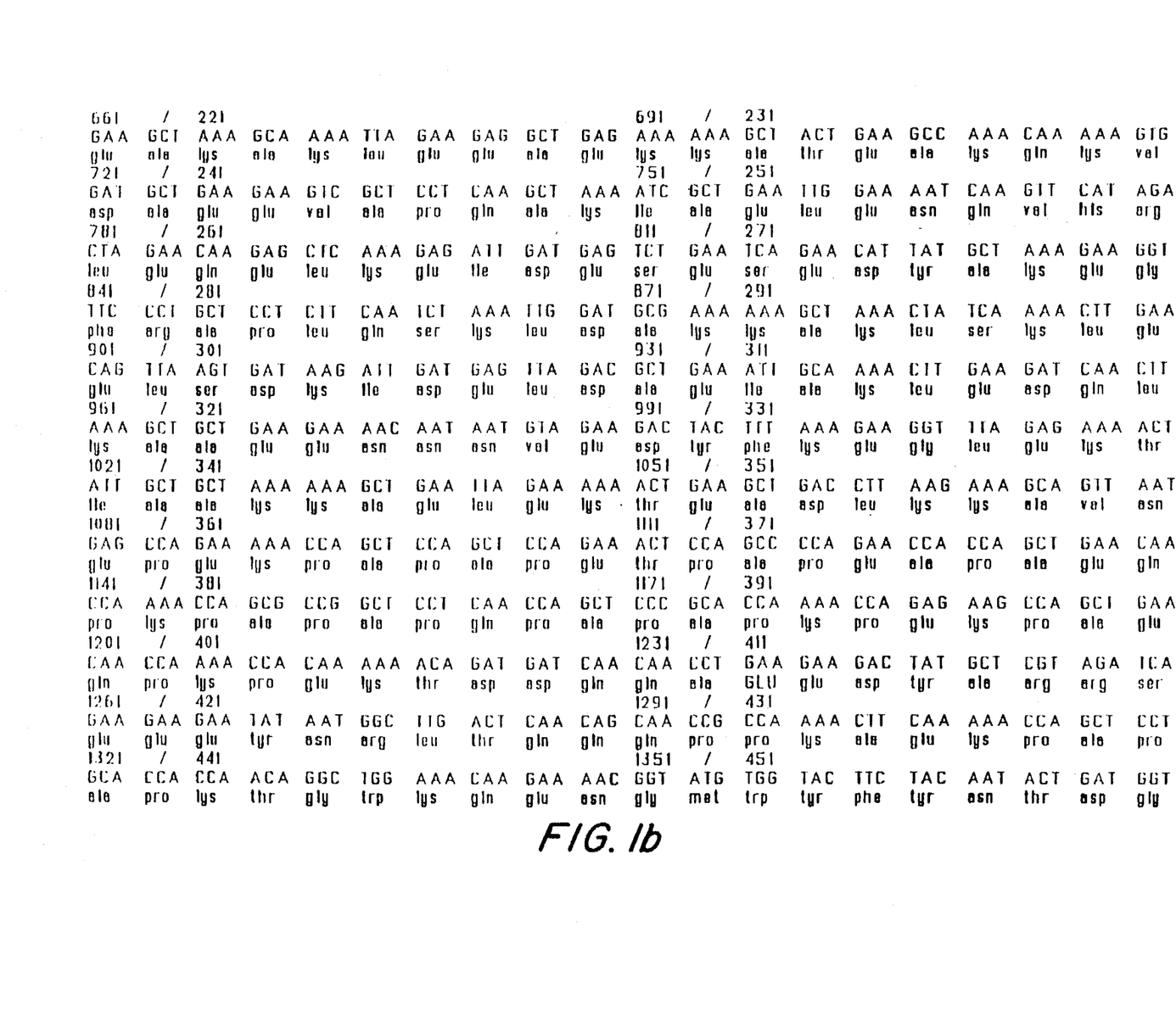
Figure 2:
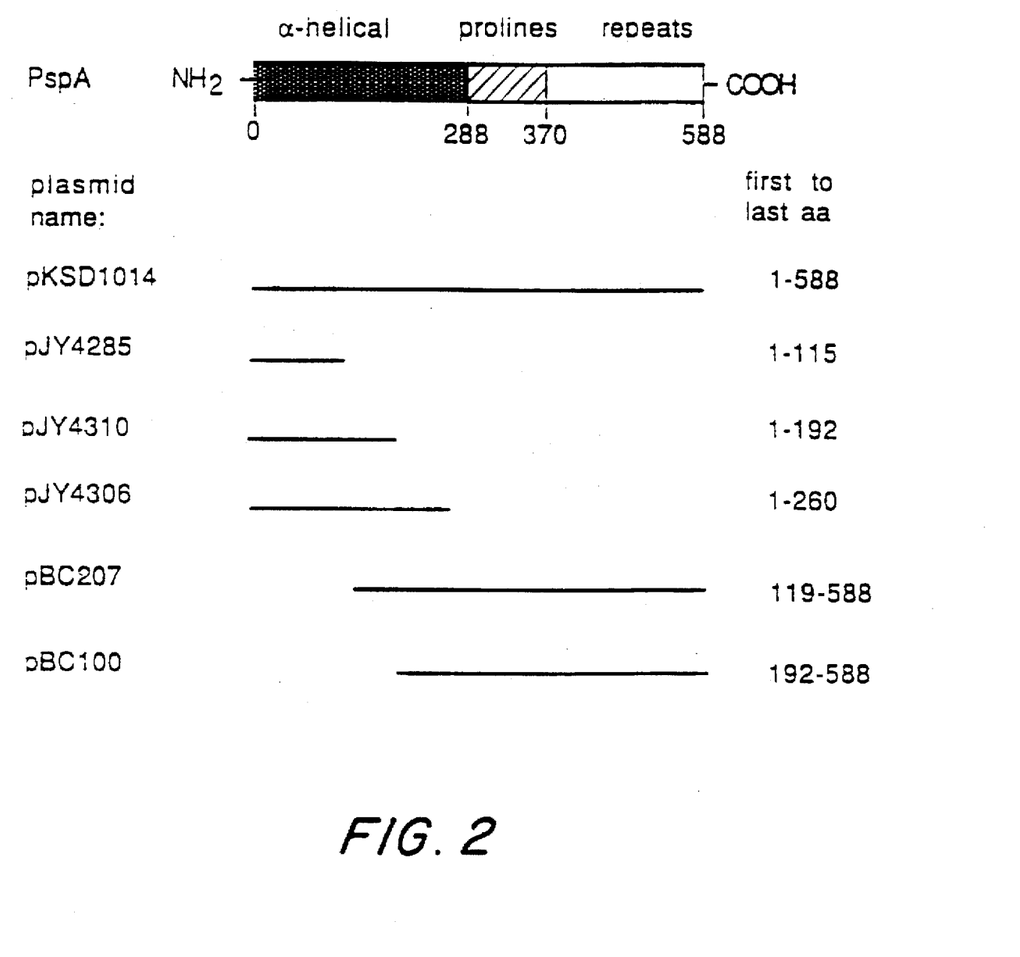
FIG. 2 contains a schematic representation of the domains of mature PspA protein as well as identification of certain plasmids containing gene sequences coding for the full length protein (pKSD 1014), coding for specific segments of the N-terminal portion of the protein (pJY4284 or pJY4285, pJY4310, pJY4306) and coding for specific sequences of the C-terminal region of the protein (pBC207, pBC100)

As described in the prior U.S. patent applications referred to above and in Yother et al (I) and (II), the pspA gene of strain Rx1 encodes a 65 kDa molecule composed of 588 amino acids. The nucleotide sequence (SEQ ID No: 1) of the pspA gene and derived amino acid sequence (SEQ ID No: 2) are set forth in FIGS. 1A–C. The N-terminal half of the molecule is highly charged and its DNA sequence predicts an α-helical coiled-coil protein structure for this region (288 amino acids), as seen in FIG. 2. The C-terminal half of PspA, which is not α-helical, includes a proline-rich region (83 amino acids) and a repeat region containing the highly conserved twenty amino acid repeats, as well as a slightly hydrophobic sequence of 17 amino acids at the C-terminus. It is known that PspA is anchored to *S. pneumoniae* by its C-terminal half and it is likely that the proline-rich region serves to tangle the molecule in the cell wall. In addition, it is anticipated that the highly-charged α-helical region begins at the cell wall and extends into and possibly through the capsule. This model is supported by the observation that the s-helical domain contains all the surface exposed epitopes recognized by monoclonal antibodies (MAbs) reactive with PspA on the pneumococcal surfaces.

The PspA protein of *S. pneumoniae* strain Rx1 has been mapped to locate protection-eliciting epitopes. Such mapping has been effected by employing antibodies to PspA protein and recombinant fragments of PspA. This mapping technique, described in detail in the Examples below, has identified an amino acid sequence corresponding to the C-terminal third of the α-helical region of PspA as containing protection-eliciting epitopes, specifically the amino acid residues 192 to 260 of the Rx1 PspA protein. The amino acid sequence from residues 192 to 260 is the C-terminal third of the α-helical sequence, expected to be near the cell wall surface.

Since the portion of the sequence from residues 192 to 260 contains only 68 amino acids, individual PspA protein fragments of this size may not be optimally antigenic. This difficulty is overcome by producing recombinant proteins containing tandem fragments of different PspAs expressed by gene fusions of the appropriate portions of several pspA genes.

Accordingly, in a further aspect of the invention, there is provided a PspA protein fragment comprising a plurality of conjugated molecules, each molecule comprising amino acid residues 192 to 260 of the PspA protein of the Rx1 strain of *Streptococcus pneumoniae* and containing at least one protection-eliciting epitope, each molecule being derived from a different strain of *S. pneumoniae*.

Such tandem molecules can be engineered to maintain proper coiled-coil structure at the points of junction and to be large enough to be immunogenic and to express an array of protection-eliciting epitopes that may cross-react with a wide spectrum of PspAs. Alternatively, individual recombinantly-produced peptides may be attached by chemical means to form a complex molecule.

A further alternative is to attach the PspA fragment to a larger carrier protein or bacterial cell, either as a recombinant fusion product or through chemical attachment, such as by covalent or ionic attachment.

The protein fragments and peptide analogs thereof provided herein are useful components of a vaccine against disease caused by pneumococcal infection. Accordingly, the present invention provides, in a yet further aspect, a vaccine comprising the PspA protein fragments defined herein as an immunologically-active component thereof.

BIOLOGICAL MATERIALS

The Examples which follow as well as in the accompanying drawings, reference is made to certain plasmid materials containing whole or truncated pspA gene sequences. The following Table II provides a summary of such materials:

TABLE II

| Plasmid | Identification | Gene Product |
|---|---|---|
| pKSD1014 | whole gene | amino acids 1 to 588 |
| pJY4284 or pJY4285 | 5' terminal region | amino acids 1 to 115 |
| pJY4310 | 5'-terminal region | amino acids 1 to 192 |
| pJY4306 | 5'-terminal region | amino acids 1 to 260 |
| pBC207 | 3'-terminal region | amino acids 119 to 588 |
| pBC100 | 3'-terminal region | amino acids 192 to 588 | have previously been described in McDaniel et al (I) and Crain et al (supra). The remaining cell lines were prepared by immunizing CBA/N mice with recombinant D39 PspA expressed in λgtII by the technique described in McDaniel et al (I). The cell lines producing antibodies to PspA were all identified using an ELISA in which microtitration plates were coated with heat-killed (60° C., 30 mins) *S. pneumoniae* R36A or Rx1, which would select for those MAbs that react with surface exposed epitopes on PspA. The heavy chain isotypes of the MAbs were determined by developing the ELISA with affinity purified goat antibody specific for μ and λ heavy chains of IgM and IgG mouse immunoglobulin. The specificity of the MAbs for PspA was confirmed by immunoblot analysis.

All six newly-produced MAbs, identified in Table III as XiR 1526, XiR 35, XiR 1224, XiR 16, XiR 1325 and XiR 1323, detected a protein of the expected size (apparent molecular weight of 84 kDa) in an immunoblot of strains Rx1 and D39. No reactivity was observed for any of the MAbs in an immunoblot of strain WG44.1, a PspN variant of Rx1 (see McDaniel et al (III) and Yother et al (II)).

TABLE III

Reactivities of MAbs with PspAs from *Streptococcus pneumoniae*

| Streptococcus pneumoniae | | | | Monocional Antibody (Isotype) | | | | | | | |
|---|---|---|---|---|---|---|---|---|---|---|---|
| Strain | Capsule type | PspA type | Ref. # | XiR1526 (IgG2b) | XiR35 (IgG2a) | XiR1224 (IgM) | Xi126 (IgG2b) | XiR16 (IgG2a) | Xi64 (IgM) | XiR1325 (IgG2a) | XiR278 (IgG1) | XiR1323 (IgM) |
| Rx1 | rough | 25 | 36 | ++ | ++ | ++ | ++ | ++ | ++ | ++ | ++ | ++ |
| ATCC101813 | 3 | 3 | 37 | − | − | − | ++ | − | ++ | ++ | ++ | ++ |
| EF10197 | 3 | 18 | 38 | − | − | − | − | − | − | −/+ | ++ | − |
| BG9739 | 4 | 26 | 38 | − | − | − | − | − | − | ++ | + | ++ |
| L81905 | 4 | 23 | 38 | − | − | − | − | − | − | − | − | − |
| BG-5-8A | 6A | 0 | 38 | − | − | + | −/+ | − | − | − | + | + |
| BG9163 | 6B | 21 | 38 | − | − | − | − | − | − | − | + | − |
| LM100 | 22 | ND | * | − | − | − | −/+ | − | − | − | − | − |
| WU2 | 3 | 1 | 39 | − | − | − | ++ | − | ++ | ++ | ++ | ++ |
| Protection against WU2 | | | | − | − | − | + | − | + | + | + | + |

EXAMPLES

Example 1

This Example describes the bacterial strains, plasmids and hybridoma antibodies used herein.

*S. pneumoniae* strains, identified in Table III below, were grown in Todd Hewitt broth with 0.5% yeast extract at 37° C. or on blood agar plates containing 3% sheep blood in a candle jar. *E. coli* strain DH1 (Hanahan, J. Mol. Biol. 166:557) was grown in LB medium or minimal E medium. Plasmids included pUC18 (Gene 33:103), pJY4163 (Yother et al (II)), and pIN-III-ompA (EMBO J. 3:2437).

All antibody-secreting hybridoma lines were obtained by fusions with non-antibody-secreting myeloma cell line P3-X63-Ag.8.653 (J. Immunol. 123:1548). The specific antibodies employed are identified in Table III below. The anti-PspA hybridoma cell lines Xi64, Xi126 and XiR278

Example 2

This Example describes the provision of the pspA gene from pneumococcal strain Rx1 by polymerase chain reaction (PCR).

PCR primers were designed based on the sequence of the pspA gene from pneumococcal strain Rx1 (see FIG. 1 SEQ ID NO: 1). The 5'-primers were LSM3 and LSM4. LSM3 was 28 bases in length and started at base 576 and LSM4 was 31 bases in length and started at base 792, and both contained an additional BamHI site. The 3' pspA primer was LSM2 which was 33 bases in length and started at base 1990 and contained an additional SalI site.

The nucleotide sequences for the primers are as follows:
LSM2 5'-GCGCGTCGACGGCTTAAACCCATTCACCA-TTGG-3' (SEQ ID NO:3)
LSM3 5'-CCGGATCCTGAGCCAGAGCAGTTGGCTG-3' (SEQ ID NO: 4)

LSM4 5'-CCGGATCCGCTCAAAGAGATTGATGAGTC-TG-3' (SEQ ID NO: 5)

Approximately 10 ng of genomic Rx1 pneumococcal DNA was amplified using a 5' and 3' primer pair. The sample was brought to a total volume of 50 µl containing a final concentration of 50 mM KCl, 10 mM tris-HCl (pH 8.3), 1.5 mM $MgCl_2$, 0.001% gelatin, 0.5 mM each primer and 200 mM of each deoxynucleoside triphosphate and 2.5 U of Taq DNA polymerase. Following overlaying of the samples with 50 µl of mineral oil, the samples were denatured at 94° C. for 2 mins and then subjected to 10 cycles consisting of 1 min. at 94° C., 2 min. at 50° C. and 3 min. at 72° C., followed by another 20 cycles of 1 min. at 94° C., 2 min. at 60° C. and 3 min. at 72° C. After completion of the 30 cycles, the samples were held at 72° C. for an additional 5 min., prior to cooling to 4° C.

Example 3

This Example describes expression of truncated PspA molecules.

3'-deleted pspAs that express N-terminal fragments in *E. coli* and which secrete the same fragments from pneumococci were constructed as described in the aforementioned U.S. patent applications Ser. Nos. 835,698 and 656,773 (see also Yother et al (II), supra).

For expression of 5'-deleted pspA constructs, the secretion vector pIN-III-ompA was used. Amplified pspA fragments were digested with BamHI and SalI and ligated into the appropriately BamHI/SalI- digested pIN-III-ompA vector, providing the inserted fragment fused to the ompA leader sequence in frame and under control of the lac promoter. Transformants of *E. coli* DH1 were selected on minimal E medium supplemented with casamino acids (0.1%), glucose (0.2%) and thiamine (0.05 mM) with 50 µg/ml of ampicillin.

Figure 4:
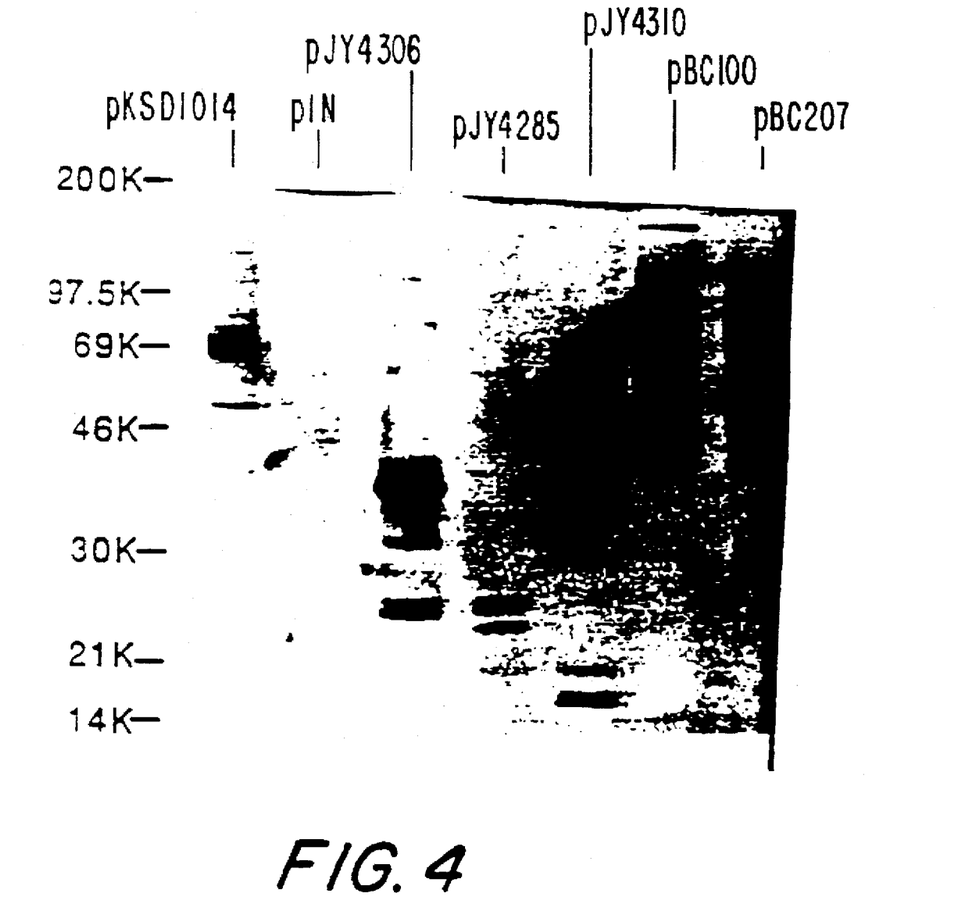
FIG. 4 is an immunoblot of PspA protein gene products produced by plasmids identified therein.

For induction of lac expression, bacteria were grown to an optical density of approximately 0.6 at 660 nm at 37° C. in minimal E medium and IPTG was added to a concentration of 2 mM. The cells were incubated for an additional two hours at 37° C., harvested and the periplasmic contents released by osmotic shock. An immunoblot of the truncated PspA proteins produced by the various plasmids is shown in FIG. 4.

By these procedures, there were provided, for the 3'-deleted pspAs, plasmids pJY4284, pJY4285, pJY4310 and pJY4306 and for the 5'-deleted pspAs, plasmids pBC207 and pBC100. Plasmid pJY4284 and pJY4285 contain an insert of 564 base pairs, nucleotides 1 to 564 and encoded a predicted 13 kDa PspA C-terminal-deleted product corresponding to amino acids 1 to 115. Plasmid pJY4310 contains an insert of 795 base pairs, nucleotides 1 to 795 and encoded a predicted 21 kDa C-terminal-deleted product corresponding to amino acid 1 to 192. However pJY4306 contained an insert of 999 base pairs, nucleotides 1 to 999 and encoded a predicted 29 kDa C-terminal-deleted product corresponding to amino acids 1 to 260. Plasmid pBC100 contained an insert of 1199 base pairs, nucleotides 792 to 1990, and encoded a predicted 44 kDa PspA N-terminal deleted product containing amino acids 192 to 588. pBC207 contained an insert of 1415 base pairs, nucleotide 576 to 1990, and encoded a predicted 52 kDa PspA N-terminal deleted product containing amino acids 119 to 588.

The pspA gene sequences contained in these plasmids code for and express amino acids as identified in FIG. 2 SEQ ID NO: 2.

Example 4

This Example describes the procedure of effecting immunoassays.

Immunoblot analysis was carried out as described in McDaniel et al (IV). The truncated PspA molecules prepared as described in Example 3 or pneumococcal preparations enriched for PspA (as described in McDaniel et al (II)) were electrophoresed in a 10% sodium dodecyl sulfate polyacrylamide gel and electroblotted onto nitrocelluloses. The blots were probed with individual MAbs, prepared as described in Example 1.

A direct binding ELISA procedure was used to quantitatively confirm reactivities observed by immunoblotting. In this procedure, osmotic shock preparations were diluted to a total protein concentration of 3 µg/ml in phosphate buffered saline (PBS) and 100 µl was added to wells of Immulon 4 microtitration plates. After blocking with 1% bovine serum albumin in PBS, unfractionated tissue culture supernates of individual MAbs were titered in duplicate by 3-fold serial dilution through 7 wells and developed as described in McDaniel et al (IV) using a goat anti-mouse immunoglobulin alkaline phosphate conjugated secondary antibody and alkaline phosphate substrate. Plates were read in a DYNATECH (trademark) plate reader at 405 nm, and the 30% end point was calculated for each antibody with each preparation.

The protective capacity of the MAbs was tested by injecting three CBA/N mice i.p. with 0.1 ml of 1/10 dilution (about 5 to 30 µg) of each hybridoma antibody 1 hr prior to i.v. injection of $10^3$ CFU of WU2 or D39 pneumococci (>100×$LD_{50}$). Protection was judged as the ability to prevent death of all mice in a group. All non-protected mice died of pneumococcal infection within 48 hours post challenge.

Example 5

This Example describes mapping of the epitopes on PspA using the monoclonal antibodies described in Example 1.

The six newly-produced monoclonal antibodies described in Example 1 and identified in Table III were used along with the previously-described monoclonal antibodies Xi64, Xi126 and XiR278 to map epitopes on PspA.

To determine whether each of the MAbs recognized different epitopes, each of them was reacted with eight additional *S. pneumoniae* strains, as identified in Table III, in immunoblots of SDS-PAGE separated proteins. Seven different patterns of activity were observed. Three antibodies, XiR16, XiR35 and XiR1526, appeared to recognize epitopes found on Rx1 PspA but none of the other PspAs. Accordingly, it was possible that these three antibodies might all react with the same epitope as Rx1 PspA.

MAb Xi64 and Xi126 both reacted strongly only with epitopes on ATCC 101813, WU2 and Rx1 PspAs, but not with PspAs of the other strains. However, it is known from studies of larger panels of PspAs (as described in McDaniel et al (III) and Crain et al) that Xi126 and Xi64 recognize different determinants.

The remaining four antibodies each exhibited unique patterns of reactivity with the panel of PspAs. Accordingly, the nine antibodies tested recognized at least seven different epitopes on PspA.

For reasons which are not clear, the type 2 strain D39 appeared to be uniquely able to resist the protective effects of antibodies to PspA (McDaniel et al (IV)). As described in McDaniel et al (I), greater than forty times the amount of Xi126 was required to passively protect against the D39 strain as compared to the WU2 strain. None of the six newly-produced monoclonal antibodies protected against the D39 strain. In contrast, immunization of mice with Rx1 PspA elicits protection against A66, WU2 and EF6796 strains (mouse virulent pneumococci of capsular types 3, 3 and 6A respectively), all of which have PspA types that are different from those of Rx1 and D39 (see McDaniel et al (IV)). In view of the close serologic similarity between the type 25 PspA of Rx1 and type 1 PspA of WU2 (Crain et al), WU2 pneumococci were used to challenge mice that had been passively protected with the MAbs. All five of the MAbs that were observed to bind WU2 PspA were able to protect against infection with 1000 CFU of WU2. Protective antibodies were found in IgM, IgG1, IgG2b and Ig2a heavy chain isotype classes.

Example 6

This Example describes mapping of the epitopes of PspA using the recombinant truncated PspA molecules formed in Example 3.

The five-overlapping C-terminal or N-terminal deleted PspA fragments, prepared as described in Example 3 and shown in FIG. 2, were used to map epitopes on PspA. The general location of the epitopes detected by each of the mice MAbs, as described in Example 5, was determined using the five C-terminal-deleted and two N-terminal deleted PspA molecules. As a positive control, the reactivity of each antibody was examined with a clone, pKSD1014, expressing full-length PspA.

As noted earlier, the reactivity of the MAb was determined by two methods. In one method, reactivity between the fragments and MAb was evaluated in immunoblots of the fragment preparations after they had been separated by SDS-PAGE. In the second method, a direct ELISA was used to quantify the reactivity of the MAbs with non-denatured PspA fragment.

The reactivities observed and the quantification of such activity is set forth in the following Table IV:

epitope(s) detected by all three lies within the first 115 amino acids of PspA. This map position is in agreement with the failure of these antibodies to react with either of the N-terminal-deleted clones that lack the first 119 and 191 amino acids.

MAbXiR1224 reacted strongly by immunoblot with the longest C-terminal-deleted fragment (pJY4306), but showed substantially weaker reactions with the shorter two C-terminal-deleted fragments. This result indicates that, while the binding site of the antibody may be in the first 115 amino acids, residues beyond amino acid 192 may be important for the conformation or stability of the epitope.

By immunblot, the three antibodies Xi64, XiR1325 and XiR278, all reacted with the longest C-terminal-deleted fragment and both of the N-terminal-deleted fragments, thus locating their determinants between amino acid positions 192 and 260. Generally confirmatory results were obtained in ELISAs with the native molecules. However, in a few cases, reactions were observed in ELISAs with full length PspA but not with a truncated molecule even though the same truncated fragment was reactive with the antibody by immunoblot. These observations may have resulted from an altered conformation of the truncated fragments under physiologic conditions that masked or prevented the formation of determinant present in full-length PspA and in the denatured fragments.

Two antibodies XiR216 and XiR1323 showed what, at first appeared to be anomalous reactions, indicating that epitopes detected by the antibodies might be in more than one portion of PspA. In view of this unexpected result, the assays were repeated multiple times with two sets of preparations of the truncated fragments. The results of the additional assays confirmed the two-position mapping of epitopes for these two MAbs.

By immunoblot, MAb XiR16 reacted strongly with the two longest C-terminal-deleted fragments and failed to react with the shortest N-terminal-deleted fragment. Accordingly, the epitope detected must be N-terminal to position 192. Unexpectedly, MAbXiR16 reacted weakly in immunoblots with both the longest N-terminal-deleted fragment (residues 119 to 158) and the shortest C-terminal-deleted fragment (residues 1 to 115). Since the fragments do not overlap, and

TABLE IV

Reactivity of PspA Fragments with Monclonal Antibodies[1]

| PspA Fragments | Monoclonal Antibodies | | | | | | | | |
|---|---|---|---|---|---|---|---|---|---|
| | Xi126 | XiR35 | XiR1526 | XiR1224 | XiR16 | XiR1323 | Xi64 | XiR1325 | XiR278 |
| pJY4285 | ++ 72 | ++ 5 | ++ <3 | + <3 | + 4 | − <3 | − <3 | − <3 | − <3 |
| pJY4310 | ++ 116 | ++ 4 | ++ <3 | + 5 | ++ 16 | − 31 | − <3 | − <3 | − <3 |
| pJY4306 | ++ 1127 | ++ 78 | ++ 554 | ++ 805 | ++ 2614 | ++ <3 | ++ 643 | ++ 717 | + <3 |
| pBC207 | − <3 | − <3 | − <3 | − <3 | + <3 | ++ 61 | ++ <3 | ++ <3 | ++ 4527 |
| pBC100 | − <3 | − <3 | − <3 | − <3 | − <3 | ++ 15 | ++ 709 | ++ 4401 | ++ 4746 |
| Rx1 | ++ 63 | ++ 15 | ++ 42 | ++ 48 | ++ 118 | ++ 44 | ++ 64 | ++ 111 | ++ 468 |
| pIN-III | − <3 | − <3 | − <3 | − <3 | − <3 | − <3 | − <3 | − <3 | − <3 |

[1]Antibodies were reacted with the indicated PspA fragments in immunoblot of SDS-PAGE separations, or by ELISA using microtitration plates coated with preparations enriched for the indicated PspA fragments. Rx1 PspA serves as a positive control, and pIN-III-ompA(vector alone) serves as a negative control. The results of the immunoblot are presented as ++ (strong reaction), + (weak but clearly positive reaction) and − (no reaction). ELISA values are given as the reciprocal dilution of each monoclonal antibody that gave 30% of maximum binding with wells coated with the indicate fragment preparation.
The asterisk (*) after some of the antibodies denotes those which are able to protect against fatal pneumococcal infection with strain WU2 or D39 *S. pneumoniae*.

Figure 3:
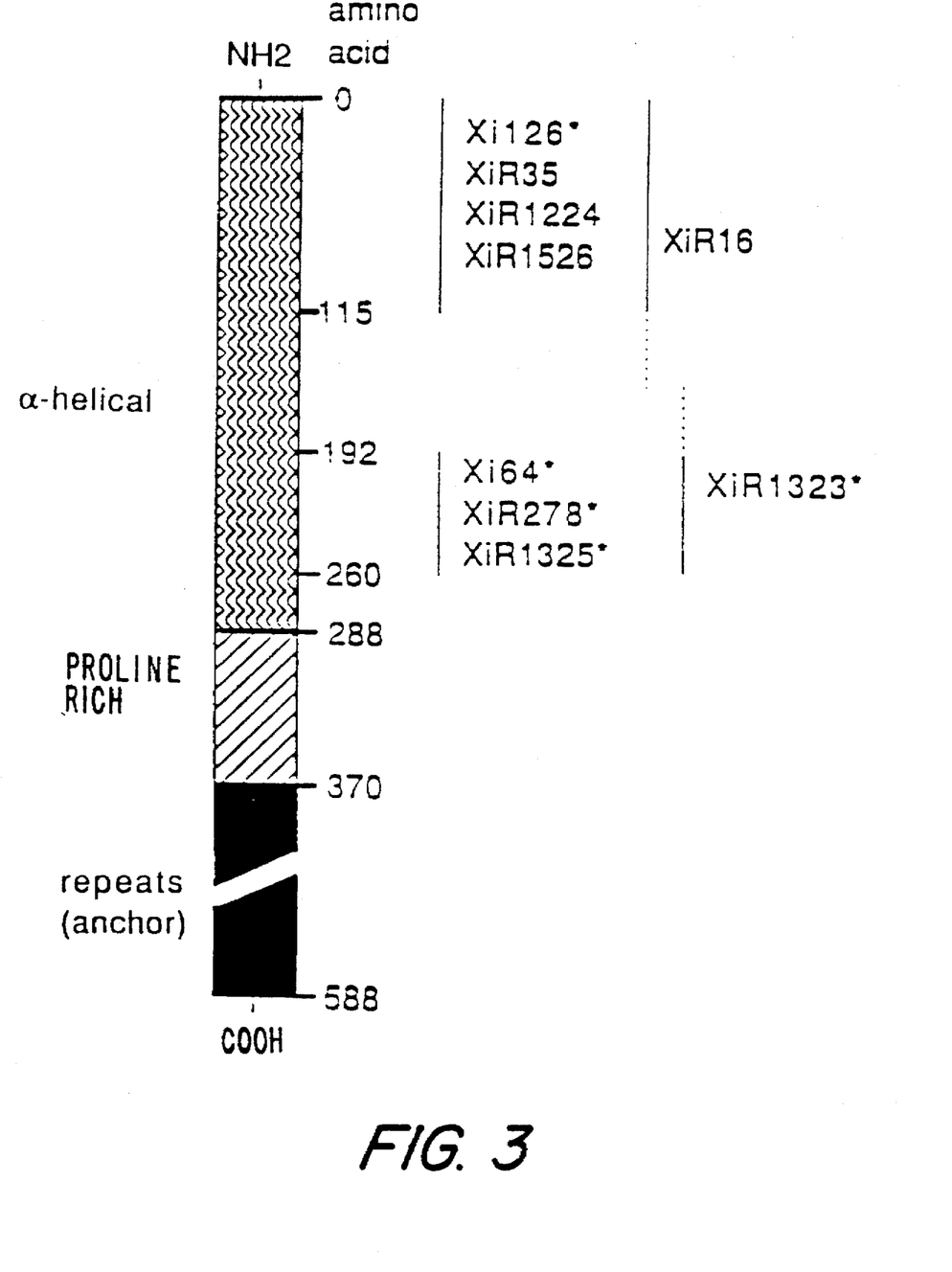
FIG. 3 contains a schematic representation of the domains of the mature PspA protein and the general location of epitopes recognized by certain monoclonal antibodies.

The deduced locations of the epitopes are indicated in FIG. 3.

As can be seen from the data in Table IV, three of the antibodies, Xi126 and XiR35 and XiR1526, react strongly with all three C-terminal-deleted clones in immunoblot analysis, indicating that the sequence required to form the if the weak immunoblot reactivities with fragments (reactivities not seen by ELISA) are not an artifact, the MAb XiR16 must recognize epitopes on both fragments.

In the case of MAb XiR1323, the immunoblot data clearly places the detected epitope between positions 192 and 260. In the ELISA studies, however, XiR1323 reacted strongly and reproducibly with the C-terminal-deleted fragment pJY4310 (amino acid residues 1 to 192) as well as the shortest N-terminal-deleted fragment pBC100 (amino acid residues 192 to 588). Curiously, an ELISA reaction was not observed between MAb XiR1323 and pJY4306 (amino acid residues 1 to 260), even though MAb XiR1323 reacted strongly with this fragment by immunoblot.

These findings provide additional evidence for distal conformation effects on antigenic determinants of PspA. They also indicate that, on the native fragments, MAb XiR1323 sees epitopes on both sides of position 192. The relationship between expression of the epitopes in other PspAs and their position in Rx1 PspA is demonstrated in Table IV in which is listed the antibodies in accordance with their apparent map position in PspA. The five antibodies (including XiR16) that clearly recognize epitopes N-terminal to position 116 are listed at the left side of Table IV. The four antibodies that clearly recognize epitopes C-terminal to position 192 are listed on the right side of Table IV. Three of the five epitopes N-terminal of position 192 (those recognized by XiR1526, XiR35, and XiR16) were not found on any of the other eight PspAs tested. One epitope (recognized by XiR 1224) was weakly expressed by one other strain and another (recognized by Xi126) was expressed on two other strains. In contrast, the four epitopes present in the C-terminal third of the PspA α-helical region were each present in from two to six other strains. The greater conservation of the region C-terminal to position 192, as compared to the region N-terminal to position 192 was significant at P<0.05 by both the Chi-square and the two sample rank tests. Based on the mapping results (Table III) and the strain distribution results (Table IV), it is apparent that all of the antibodies except possibly XiR35 and XiR1526 must recognize different PspA determinants.

Example 7

This Example contains a discussion of the mapping results achieved in Example 6.

The results set forth in Example 6 clearly demonstrate that the protection eliciting epitopes of PspA are not restricted to the N-terminal end of the surface exposed α-helical half of the molecule. In fact, four of the five antibodies protective against *S. pneumoniae* WU2 reacted with the C-terminal third of the α-helical region of PspA. This portion of the α-helical region is thought to closest to the cell wall (see Yother et al (II)).

About half of the MAbs recognized determinants N-terminal to amino acid 115 and the other half recognized epitopes C-terminal to residue 192. Since the nine antibodies were selected for their ability to bind native PspA on the surface of heat-killed whole pneumococci, the distribution of the epitopes they recognize suggests that determinants between positions 115 and 192 are either not immunogenic or are not exposed on the native molecule as expressed on pneumococci.

Curiously two MAbs (XiR16 and XiR1323) appeared to possibly react with epitopes in more than one position on PspA. Although the bulk of the data for XiR16 placed its epitope N-terminal of position 115, weak immunoblot patterns suggested that a reactive epitope(s) may also exist C-terminal to residue 115. In the case of XiR1323, the bulk of the data indicated that its epitope is between positions 192 and 260. However, the ELISA assay showed significant reactivity of the antibody with a C-terminal-deleted PspA fragment extending from residues 1 to 192. Although there are no extensive repeats in the N-terminal half of PspA, there are a few short repeated sequences that occur more than once in the coiled-coil motif. One such sequence is glu-glu-ala-lys which starts at amino acid positions 156, 164, and 178 and another is lys-ala-lys-leu starting at positions 181 and 251 (see FIG. 1). In the case of XiR1323, the antibody reacted with the epitope on the 1 to 192 fragment under natured but not denatured conditions. This may indicate that the epitope is conformational and may not have the same exact sequence as the epitope recognized (under both natured and denatured conditions) between residues 192 and 260.

One mechanism that may account for the lack of exposure of epitopes between amino acid 115 and 192 would be a folding back of this portion of the α-helical sequence on itself or other parts of PspA to form a coiled-coil structure more complex than a simple coiled-coil dimer. If this occurred, it could explain how PspA tertiary structure can sometimes be dependent on distant PspA structures. A suggestion that this might, in fact, be the case comes from the observation that some of the truncated forms did not express certain epitopes under physiologic conditions that were detected on the whole molecule under the same conditions and were shown to be present in the fragment after denaturation in SDS.

Since a PspA vaccine may need to contain fragments of several serologically different PspAs, it would be desirable to include in a vaccine only those portions of each PspA that are most likely to elicit cross-protective antibodies. Based on the results presented herein with Rx1 PspA, it appears likely that the portion of the PspA sequences corresponding to residues 192 to 260 of Rx1 PspA is the best portion of PspA to include in a recombinant PspA vaccine. The epitopes in this portion of PspA were three and a half times as likely to be present in the PspAs of other strains as the epitopes in the residue 1 to 115 portion of the sequence, and none of the 9 antibodies studied clearly reacted with the middle third of the α-helical region.

Example 8

This Example shows protection of mice by PspA fragments. Five mice were immunized with purified fragment produced by pBC207 in *E. coli* and five with purified fragment produced by pBC100 in *E. coli*. In both cases, the fragments were injected in Freund's complete adjuvant. All mice immunized with each fragment survived challenge with 100×LD$_{50}$ of WU2 capsular type 3 *S.pneumoniae*.

Five additional mice were injected with adjuvant plus an equivalent preparation on non-PspA producing *E. coli*. All mice died when challenged with the same dose of WU2.

The data presented in this Example conclusively proves that epitopes C-terminal to amino acids 119 and 192 respectively are capable of eliciting protective immunity. This result is consistent with the findings presented in the earlier Examples that the region of PspA from amino acids 192 to 260 contain protection-eliciting epitopes.

SEQUENCE IDENTIFICATIONS

SEQ ID NO: 1 DNA sequence for pspA gene (FIG. 1)
SEQ ID NO: 2 Deduced amino acid sequence for PspA protein (FIG. 1)
SEQ ID NO: 3 Nucleotide sequence for PCR primer LSM 2
SEQ ID NO: 4 Nucleotide sequence for PCR primer LSM 3
SEQ ID NO: 5 Nucleotide sequence for PCR primer LSM 4

SUMMARY OF THE DISCLOSURE

In summary of this disclosure, the present invention provides a PspA protein fragment which contains protection-eliciting epitopes and which is cross-reactive and can be incorporated into a vaccine against disease caused by pneumococcal infection. Modifications are possible within the scope of this invention.

What we claim is:

1. An isolated pneumoccal surface protein A (PspA) fragment comprising amino acid residues 192 to 260 of full length PspA of Streptococcus pneumoniae, wherein said fragment contains at least one immune responsive-eliciting epitope.

2. The isolated PspA fragment of claim 1 which was produced recombinantly in the form of a protein which was truncated from the C-terminal.

3. The isolated PspA protein fragment of claim 2 which contains one-third of said C-terminal and an α-helical region of full length PspA.

4. A PspA fragment comprising a plurality of conjugated molecules, wherein each molecule comprises amino residues 192 to 260 of full length PspA of Streptococcus pneumoniae, wherein said molecule contains at least one immune responsive-eliciting epitope, and each molecule is from a different strain of Streptococcus pneumoniae.

5. The PspA fragment of claim 4 wherein each of said molecules has the amino residues 192 to 260 of full length PspA of the Rx1 strain of Streptococcus pneumoniae as set forth in SEQ ID No. 2.

6. The PspA fragment of claim 5 wherein each of said molecules is produced recombinantly in the form of protein which is truncated from the C-terminal end of the full length PspA.

7. The isolated PspA fragment of claim 1 consisting of said acid residues 192 to 260 of full length PspA.

8. An isolated PspA fragment comprising amino residues 192 to 260 of full length PspA, and containing at least one immune responsive-eliciting epitope, wherein said fragment reacts with a monoclonal antibody which reacts with an isolated PspA fragment comprising amino residues 192 to 260 of full length PspA of the Rx1 strain of Streptococcus pneumoniae as set forth in SEQ ID No. 2.

9. The isolated PspA fragment of claim 8 consisting of said acid residues 192 to 260 of full length PspA.

10. The isolated PspA fragment of claim 1 which was produced recombinantly in the form of protein which was truncated from the N-terminal end of the full length PspA.

11. The PspA fragment of claim 5 wherein each of the molecules is produced recombinantly in the form of protein which is truncated from the N-terminal end of the full length pspA.

* * * * *

UNITED STATES PATENT AND TRADEMARK OFFICE
CERTIFICATE OF CORRECTION

PATENT NO. : 5,679,768
DATED : October 21, 1997
INVENTOR(S) : Briles et al.

It is certified that error appears in the above-indentified patent and that said Letters Patent is hereby corrected as shown below:

IN THE CLAIMS:

Claim 2, line 3: after "C-terminal" please insert --end of the full length PspA--.

Claim 11, line 4: please change "pspA" to --PspA--.

Signed and Sealed this

Sixth Day of January, 1998

Attest:

BRUCE LEHMAN

Attesting Officer

Commissioner of Patents and Trademarks